United States Patent [19]

Yan et al.

[11] Patent Number: 5,587,273

[45] Date of Patent: Dec. 24, 1996

[54] MOLECULARLY IMPRINTED MATERIALS, METHOD FOR THEIR PREPARATION AND DEVICES EMPLOYING SUCH MATERIALS

[75] Inventors: Mingdi Yan; John F. W. Keana; Martin N. Wybourne, all of Eugene, Oreg.; Christophe J. P. Sevrain, Ridgefield, Wash.

[73] Assignees: Advanced Microbotics Corporation, Portland; State of Oregon Acting by and through the State Board of Higher Education on Behalf of the University of Oregon, Eugene, both of Oreg.

[21] Appl. No.: 476,918

[22] Filed: Jun. 7, 1995

Related U.S. Application Data

[63] Continuation-in-part of Ser. No. 267,851, Jun. 23, 1994, which is a continuation of Ser. No. 6,453, Jan. 21, 1993, abandoned.

[51] Int. Cl.⁶ ........................................................ G03C 5/00
[52] U.S. Cl. .......................... 430/269; 430/296; 430/942; 356/361
[58] Field of Search .................................. 430/269, 296; 430/942; 356/361

[56] References Cited

U.S. PATENT DOCUMENTS

| | | | |
|---|---|---|---|
| 4,987,032 | 1/1991 | Miyasaka et al. | 428/411.1 |
| 5,051,312 | 9/1991 | Allmér | 428/458 |
| 5,110,833 | 5/1992 | Mosbach | 521/50 |
| 5,128,170 | 7/1992 | Matsuda et al. | 427/2 |
| 5,217,492 | 6/1993 | Guire et al. | 623/11 |
| 5,240,747 | 8/1993 | Matsuda et al. | 427/512 |
| 5,258,041 | 11/1993 | Guire et al. | 623/33 |
| 5,286,364 | 2/1994 | Yacynych et al. | 204/418 |
| 5,310,648 | 5/1994 | Arnold et al. | 435/5 |
| 5,342,646 | 8/1994 | Kleese et al. | 427/2.1 |

*Primary Examiner*—Mark Chapman
*Attorney, Agent, or Firm*—Klarquist Sparkman Campbell Leigh & Whinston, LLP

[57] ABSTRACT

A molecularly imprinted substrate and sensors employing the imprinted substrate for detecting the presence or absence of analytes are described. One embodiment of the invention comprises first forming a solution comprising a solvent and (a) a polymeric material capable of undergoing an addition reaction with a nitrene, (b) a crosslinking agent (c) a functionalizing monomer and (d) an imprinting molecule. A silicon wafer is spincoated with the solution. The solvent is evaporated to form a film on the silicon wafer. The film is exposed to an energy source to crosslink the substrate, and the imprinting molecule is then extracted from the film. The invention can be used to detect an analyte by forming films which are then exposed to a reaction energy to form a crosslinked substrate. The imprinting molecules are extracted from the crosslinked substrate. The film is exposed to one or more of the imprinting molecules for a period of time sufficient to couple the imprinting molecules to the film. The presence of the molecules is then detected. The invention also provides a molecularly imprinted polymeric material and sensors employing the molecularly imprinted polymeric material.

47 Claims, 5 Drawing Sheets

10 μm

PROUS POLYMER WITH MOLECULAR IMPRINT FOR ANALYTE

MOLECULARLY IMPRINTED MATERIALS, METHOD FOR THEIR PREPARATION AND DEVICES EMPLOYING SUCH MATERIALS

ACKNOWLEDGEMENT OF GOVERNMENT SUPPORT

This invention was made with U.S. government support under grant number GM 27137 from the National Institute of General Medical Sciences and grant number N00014-92-J-1412 (R&T code 413t011) from the Office of Naval Research. The U.S. government may have certain rights in the invention.

CROSS REFERENCE TO RELATED APPLICATIONS

This application is a continuation-in-part of U.S. patent application Ser. No. 08/267,851, entitled "CHEMICAL FUNCTIONALIZATION OF SURFACES," filed on Jun. 23, 1994, which was a file-wrapper continuing application of U.S. patent application Ser. No. 08/006,453, filed on Jan. 21, 1993, now abandoned. These prior applications are incorporated herein by reference.

FIELD OF THE INVENTION

The present invention concerns molecularly imprinted materials, particularly organic polymers, methods for preparing such materials and devices made therefrom.

BACKGROUND OF THE INVENTION

The surfaces of polymeric materials have been modified previously. See, for instance, Braybrook et al., *Prog. Polym. Sci.* 15:715–734 (1990). Previous research principally has been directed to developing novel composites [Baum et al., *Chem. Mater.* 3:714–720 (1991)] biosensors [Pantano et al., *J. Am. Chem. Soc.* 113:1832–1833 (1991)] and biomaterials [Allcock et al., *Chem. Mater.* 3:450–454 (1991)]. Surface modification also has been combined with photolithography to spatially direct the synthesis of peptides or oiigonucleotides, Fodor et al., *Science* 251:767–773 (1991) and Kiederowski, *Angew. Chem. Int. Ed. Eng.* 30:822–823 (1991); and immobilization of biopolymers. Rozsnyai et al., *Angew. Chem. Int. Ed. Eng.* 31:759–761 (1992). Most of the surface modification processes known in the art involve sequential treatment of surfaces with chemical reagents, Id., and only a few such studies have involved the use of azides as surface-modification reagents. Breslow, in Scriven (ed.) *Azides and Nitrenes*, chapter 10, Academic Press, New York (1984); Harmer, *Langmuir* 7:2010–2012 (1991).

Examples of existing methods for modifying polymer films include sulfonation of polystyrene, Gibson et al., *Macromolecules* 13:34 (1980); sulfonation of poly(aryloxy)phosphazenes, Allcock et al., *Chem. Mater.* 3:1120 (1991); plasma treatment of polyester, Porta et al., *Chem. Mater.* 3:293 (1991); base hydrolysis of polyimide, Lee et al., *Macromolecules* 23:2097 (1990); base hydrolysis of polyphosphazenes, Allcock et al., *Chem. Mater.* 3:1441 (1991); and base treatment of poly(vinylidene fluoride), Dias et al., *Macromolecules* 17:2529 (1984).

Another conventional method for modifying polymers comprises exposing the surface of a hydrocarbon polymer such as polyethylene with nitrene or carbene intermediates generated in the gas phase. Breslow, in Scriven (ed.), *Azides and Nitrenes*, chapter 10, Academic Press, New York (1984). Also, difluorocarbene generated in solution has been reported to modify 1,4-polybutadienes. Siddiqui et al., *Macromolecules* 19:595 (1986).

Perfluorophenyl azides (PFPAs) have been shown to exhibit improved CH-insertion efficiency over their non-fluorinated analogues when the PFPAs were photolyzed in hydrocarbon solvents such as cyclohexane or toluene. Keana et al., *Fluorine Chem.* 43:151 (1989); Keana et al., *J. Org. Chem.* 55:3640 (1990); Leyva et al., *J. Org. Chem.* 54:5938 (1989); and Soundararajan et al., *J. Org. Chem.* 55:2034 (1990). PFPAs were initially developed as efficient photolabeling reagents. Cai et al., *Bioconjugate Chem.* 2:38 (1991); Pinney et al., *J. Org. Chem.* 56:3125 (1991); and Crocker et al., *Bioconjugate Chem.* 1:419 (1990). Recently, bis-(PFPA)s have been shown to be efficient cross-linking agents for polystyrene, Cai et al., *Chem. Mater.* 2:631 (1990); and poly(3-octylthiophene), Cai et al., *J. Molec. Electron.* 7:63 (1991).

Molecular imprinting methods also are known. See, for instance, *Molecular Imprinting, Macromol Chem.*, 187:687 (1981). Molecular imprinting creates specific recognition sites in materials, such as polymeric organic materials. Known molecular imprinting techniques involve crosslinking materials in the presence of a functional monomer or mixture of monomers. The imprinting molecule interacts with a complementary portion of a functional monomer, either covalently or by other interactions such as ionic, hydrophobic or hydrogen bonding, so that recognition sites for the imprinting molecule can be provided in the substrate material. The imprinting molecule is then removed from the substrate to leave the recognition site. Some of these imprinting methods have been patented. For instance, Mosbach's U.S. Pat. No. 5,110,883 describes the preparation of synthetic enzymes and synthetic antibodies by molecular imprinting techniques.

Previous methods have failed to provide molecularly imprinted thin, substantially defect free films that can be used for the manufacture of sensor devices. Most known techniques begin with monomeric materials that are polymerized during the imprinting process. It has proven virtually impossible to control the production of acceptably thin films by these known processes.

Sensors ostensibly designed for medical applications, currently are receiving considerable attention. The methods used for detecting analytes with such sensors are many and varied. See, for instance, Janata et al.'s *Anal. Chem.*, 66:207 (1994). Molecular imprinting recently has been shown to be a useful means for sensing the presence of certain materials. Mosbach, *Trends Biochem. Sci.*, 19:9 (1994). However, the limitations imposed on the thickness of the film and the defects provided therein by known methods have substantially limited the capability to use such materials for the detection of plural analytes using a single sensor.

SUMMARY OF THE INVENTION

The present invention provides novel molecularly imprinted polymers and methods for making such polymers. The imprinted molecules allow the manufacture of thin films disposed on surfaces, such as the surface of a silicon wafer. The present invention solves many of the problems associated with known techniques.

One embodiment of the present invention comprises a method for molecularly imprinting a material. The method comprises forming a solution comprising a solvent and (a) a polymeric material capable of undergoing an addition reaction with a nitrene, (b) a crosslinking agent, (c) a functionalizing monomer, and (d) an imprinting molecule. This solution is placed on a substrate, such as by spincoating a film of the solution onto a silicon wafer. The solvent is then removed, such as by evaporating the solvent if it is sufficiently volatile. The residue is then exposed to an energy source, which may be selected, without limitation, from a group consisting of energized electrons, energized ions, photons, and heat, particularly ultraviolet light or an electron beam. The exposing step forms a crosslinked polymeric substrate. The imprinting molecule is then removed, such as by cleaving covalent bonds or by extraction techniques, from the crosslinked substrate.

The crosslinking agent typically, but not necessarily, satisfies the formula

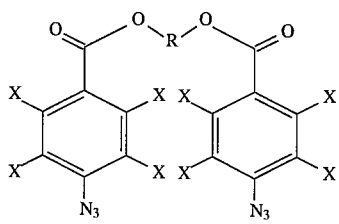

wherein X is halogen and R is lower alkyl, lower alkenyl or lower alkynyl. A preferred halogen is fluorine. The functionalizing monomer generally, but not necessarily, satisfies the formula

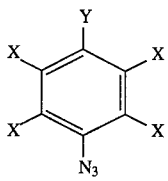

wherein X is a halogen and Y is selected from the group consisting of —OH, —ROH, —SH, —RSH, —CHO, —COOH, COOR, $NO_2$, —$NH_3$, —$NHR_1$ and —$NR_1R_2$. A working prototype of the invention has been accomplished using theophylline as the imprinting molecule.

The method also may comprise exposing preselected regions on the polymeric material to the energy source. This creates a pattern of functionalized regions on the surface relative to non-functionalized regions.

A preferred embodiment of the invention for forming materials having recognition sites for analytes comprises first forming a solution comprising a solvent and (a) a polymeric material capable of undergoing an addition reaction with a nitrene, the polymeric material being selected from the group consisting of saturated polyolefins, acrylics, polystyrene, polystyrene analogs, unsaturated polyolefins, polyimides, polyesters, conjugated polymers, conducting polymers, inorganic polymers, organometallic polymers, and polysaccharides, (b) a crosslinking agent according to the formula

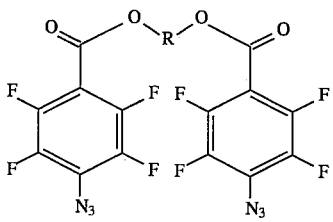

wherein R is a lower alkyl group, lower alkenyl group, or lower alkynyl group, (c) a functionalizing monomer according to the formula

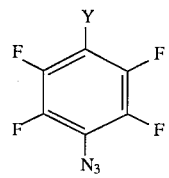

wherein Y is selected from the group consisting of —OH, —ROH, —SH, —RSH, —CHO, —COOH, COOR, $NO_2$, —$NH_3$, —$NHR_1$ and —$NR_1R_2$, and (d) an imprinting molecule. A silicon water is then spincoated with the solution. The solvent is evaporated, thereby forming a film on the silicon wafer. The film is exposed to an energy source selected from the group consisting of energized electrons, energized ions, photons and heat to crosslink the substrate. The imprinting molecule then is removed from the film.

The invention also provides a method for detecting an analyte. The method comprises forming solutions comprising (a) a substrate capable of undergoing an addition reaction with a nitrene, (b) a crosslinking agent according to the formula

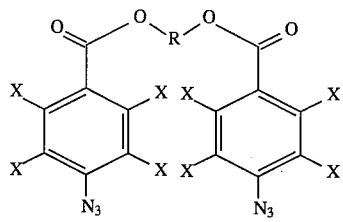

wherein R is a lower alkyl group, lower alkenyl group, or lower alkynyl group, and X is a halogen, (c) a functionalizing monomer according to the formula

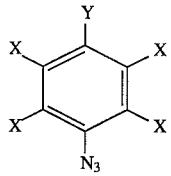

wherein X is a halogen and Y is selected from the group consisting of —OH, —ROH, —SH, —RSH, —CHO, —COOH, COOR, $NO_2$, —$NH_3$, —$NHR_1$ and —$NR_1R_2$, and (d) an imprinting molecule. The solvent is evaporated to form a film, which is then exposed to a reaction energy to form a crosslinked substrate. The imprinting molecules are extracted from the crosslinked substrate. The film is exposed to one or more of the imprinting molecules for a period of time sufficient to couple the imprinting molecules to the film. The presence of the molecules is then detected. The step of detecting the imprinting molecule may comprise measuring the capacitance of the film after the exposing step, measuring light characteristics of the film, or analyzing the film spectroscopically.

The invention also provides a molecularly imprinted polymeric materials as described above. The films of the present invention can be used to form sensor, such sa sensors for detecting therapeutics or drugs of abuse. One embodiment of such a sensor can include a film that has been imprinted with one or more imprinting molecules. The imprinted film is spincoated onto a silicon wafer to provide imprinted polymeric materials situated between plus and minus plates of a capacitor. A change in capacitance is detected upon coupling an analyte to the imprinted film.

DETAILED DESCRIPTION OF THE PREFERRED EMBODIMENTS

Figure 1:
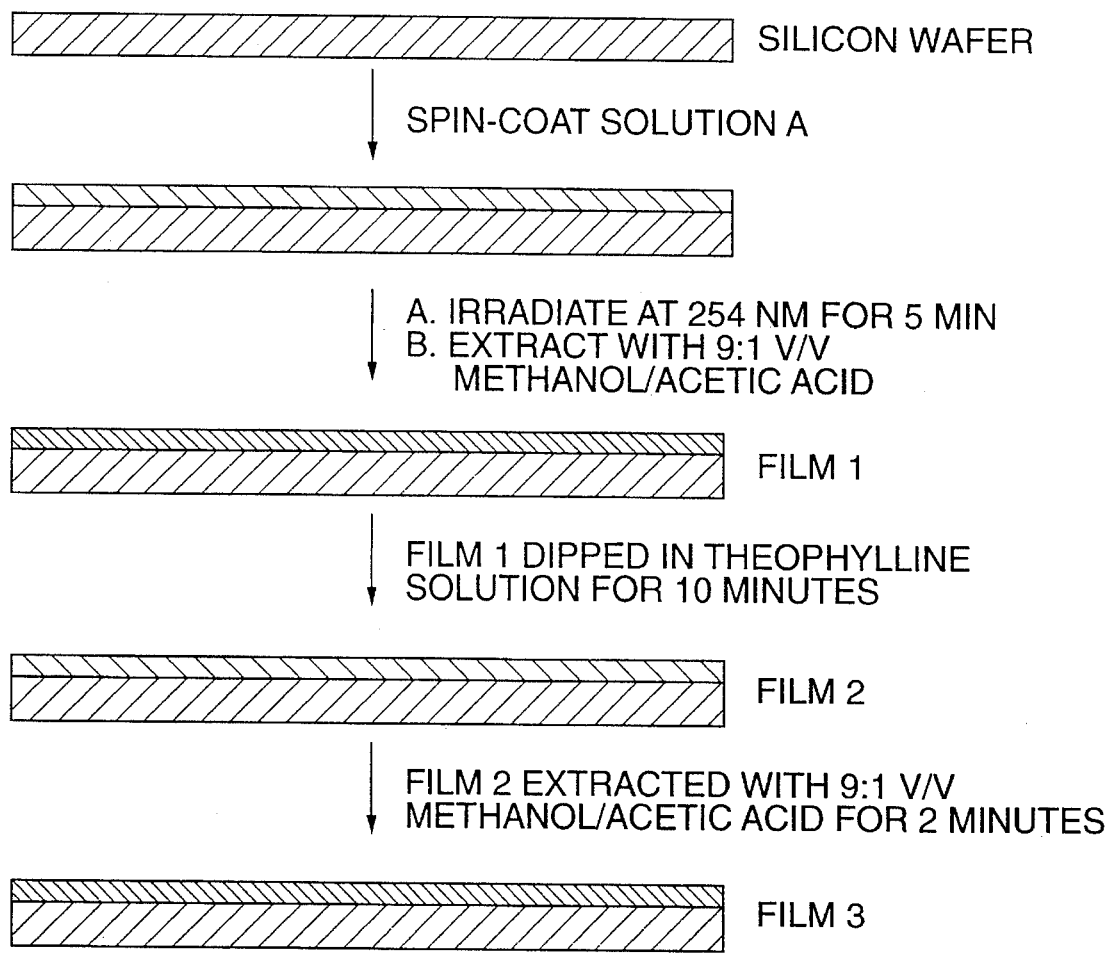
FIG. 1 is a schematic drawing representing one method for spincoating a silicon wafer with the imprinted substrates according to the present invention.

The present invention provides a method for molecularly imprinting polymeric materials and sensors made from such imprinted molecules. As used herein, molecularly imprinting refers to a process whereby molecules first are incorporated into a material, either covalently or by other interactions such as hydrogen bonding, and then removed to provide structural and reactive recognition sites in the material. For instance and without limitation, analytes may be reversibly coupled to a polymeric substrate during the crosslinking of the substrate to provide a structural recognition site. The structural recognition site also generally includes moieties that interact, either covalently or by other means, with the analyte. The analyte is then removed from the substrate to provide an analyte recognition site in the substrate that can react with analyte molecules that come into an effectively close proximity to the recognition site. The analyte interacts with the recognition site. This can be detected by, for example, a capacitance change or a change in spectral properties. The present invention provides a method for preparing such materials using a virtually unlimited number of recognition sites formed from a virtually unlimited number of analytes.

The present invention is particularly directed to crosslinking polymeric organic substrates in the presence of a crosslinking agent that includes at least two azide groups separated by a spacer. Polymeric materials, as opposed to monomer precursors of the polymeric material, are crosslinked using the azide compounds in the presence of a functional monomer that can couple with an imprinting molecule either covalently or by other non-covalent means. The functional monomer also preferably comprises an azide, or polyazide compound, that can couple with the polymeric material, such as by an insertion reaction, so as to fixedly couple the functional monomer to the polymeric substrate. The imprinting molecule is temporarily held in place by the functional monomer until it is removed by cleaving the covalent bonds that couple the imprinting molecule to the functional monomer, or by disrupting the non-covalent interactions that couple the functional monomer to the imprinting molecule.

The following provides a detailed discussion of materials used to practice the method of the invention, including: substrates, particularly polymeric organic materials; crosslinking agents; functional monomers, both covalent and noncovalent compounds; and imprinting molecules. Also described in more detail below are methods for incorporating various analytes into the substrate and subsequently removing the analytes to form recognition sites. Sensors employing these materials also are described.

I. DEFINITIONS

Certain terms used in this application may be unfamiliar, and therefore definitions of these terms are provided below. These definitions should not be construed to limit the terms to the specific definitions provided; rather, the definitions should be considered as being illustrative of the meaning typically associated with each such term.

A "substrate" is a material that can be functionalized according to the present invention. A substrate can comprise molecules (e.g., thermoplastic polymer molecules), a thermoset molecular network cross-linked polymer molecules), or other atomic or molecular association such as found in certain glasses and crystals.

A "surface molecule" is a substrate molecule having at least a portion thereof present on the substrate surface.

A "polymeric substrate" is a substrate comprising polymer molecules or a network of polymer molecules.

A "polymer molecule" is a molecule formed by covalent joining smaller molecules, termed "monomers," into molecular arrays. The monomers present in a polymer molecule can be the same or different. Polymer molecules can be natural, such as (but not limited to) cellulose, starch, proteins, and nucleic acids; or synthetic such as (but not limited to) nylon and polyethylene. In a substrate, polymer molecules can be associated with each other in any of several ways, including non-covalently (as a thermoplastic) or a covalently cross-linked network (as a thermoset).

A "functionalized substrate" is a substrate to which one or more functional groups are bonded, generally covalently, according to the present invention.

A "functional group" is a group of one or more atoms bonded together in an organized way so as to have a desired chemical property. According to the present invention, functionalizing reagents functional group can, when covalently bonded to a substrate surface according to the present invention, participate in one or more additional bonding reactions with either a similar functional group or a different type of functional group. Such bonding reactions can result in: (a) attachment to the functional groups of any of a variety of additional functional groups; or (b) coupling together (cross-linking) of the functionalized substrate molecules.

The term "functionalized polymer" can pertain to either a functionalized polymeric substrate or a functionalized polymer molecule.

A "functionalizing reagent" according to the present invention is a reagent adapted for functionalizing a substrate according to the present invention. Molecules of functionalizing agents have at least one nitrenogenic group (as a first functional group) coupled to a second functional group, wherein the nitrenogenic group is preferably constrained by the functionalizing-reagent molecular structure between the nitrenogenic group and the functional group The nitrenogenic groups are capable under reaction conditions of functionalizing a substrate surface.

A "nitrenogenic group" on a functionalizing reagent is a chemical moiety that, when exposed to a reaction-energy source, becomes a nitrene group.

A "nitrene group" (also generally termed "nitrene" or "nitrene intermediate") is a particular form of nitrogen group that can be depicted as a singlet by the structure: R-$\underline{\bar{N}}$, and as a triplet by the structure: R-$\underline{N}$ . Nitrenes are regarded by persons skilled in the art as the nitrogen analogs of carbenes. Like carbenes, nitrenes are generally regarded as intermediates. Nitrenes are highly reactive and generally cannot be isolated under ordinary conditions. However, certain chemical reactions such as reactions according to the present invention would not otherwise be explainable by known reaction mechanisms without the presumed existence of nitrenes. Important nitrene reactions can be summarized by the following:

(a) Nitrenes, including aryl nitrenes, can undergo addition reactions at —CH sites and at —NH sites; e.g.:

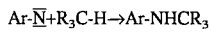

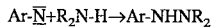

(b) Nitrenes can also undergo addition at —C—C— and —C=C— bonds; e.g.:

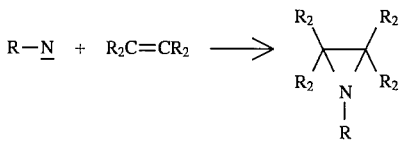

As used herein, the term "addition reaction" when used in the context of reactions of the nitrene group of the functionalizing reagent with surface molecules, generally refers to any of the various addition and insertion reactions that nitrenes can undergo with molecules on the substrate surface according to the present invention.

According to the present invention, a functionalizing reaction occurs when a functionalizing reagent comprising a nitrenogenic group is exposed to a reaction-energy source, which converts the nitrenogenic group to a nitrene intermediate. The functionalizing reaction proceeds by reaction of the nitrene intermediate with the substrate surface.

A "reaction-energy source" is an energy source that drives a functionalizing reaction according to the present invention by, in particular, converting nitrenogenic groups on functionalizing reagent molecules to nitrenes which react with the substrate surface. Suitable reaction-energy sources include (but are not limited to): photons (such as ultraviolet (UV) light, deep-UV light, laser light, X-rays, and heat in the form of infrared radiation or conductive heating), energized electrons (such as an electron beam), and energized ions (such as an ion beam). These reaction-energy sources are conventionally used for such tasks as lithography, scanning microscopy, and, in the case of UV and visible photons, effecting photochemical reactions and excitation of fluorescent molecules.

A "functionalizing reaction" is a reaction in which a substrate surface is functionalized according to the present invention. A functionalizing reaction can consist of one or more stages. At least one stage involves the reaction in the presence of a reaction-energy source of the substrate surface with molecules of a functionalizing reagent comprising nitrenogenic groups.

II. MATERIALS

A. Substrates

Generally, the materials used to form recognition sites for the imprinting molecules are polymeric materials that are capable of reacting with nitrenes. Polymeric materials that are useful for forming substrates for the imprinting molecules, include, but are not limited to:

(a) saturated polyolefins as exemplified by polyethylene, polyvinyl chloride, polytetrafluoroethylene, polypropylene, polybutenes, and copolymers thereof;

(b) acrylic resins such as polymers and copolymers of acrylic acid, methacrylic acid [poly(methylmethacrylate), poly(hexylmethacrylate)], and acrylonitrile;

(c) polystyrene and its analogues such as poly (p-chlorostyrene) and poly (p-hydroxystyrene);

(d) unsaturated polyolefins such as poly (isoprene) and poly (butadiene);

(e) polyimides such as polyimide(benzophenone tetracarboxylic dianhydride/tetraethymethylenedianiline);

(f) polyesters such as poly(trimethylene adipate) and poly(hexymethylene sebacate);

(g) conjugated and conducting polymers such as poly(3-alkylthiophene), poly(3-alkylpyrrole), and polyaniline;

(h) inorganic polymers such as poly(aryloxyphosphazene), poly[bis(trifluoroethoxy)phosphazene], polysilanes, and polycarbosilanes, siloxane polymers, and other silicon-containing polymers;

(i) organic metals (i.e., organic polymers with metallic properties) such as polycroconaines and polysquaraines, as described in *Chemical and Engineering News* (Aug. 31, 1992), p.8.

(j) organometallic polymers such as palladium poly-yne and ferrocene-containing polyamides; and (k) polysaccharides such as cellulose fibers, chitin, and starch.

B. Crosslinking Agents

The substrates discussed above are crosslinked using a crosslinking agent in the presence of a functional monomer and an imprinting molecule. The crosslinking agents typically include two or more nitrenogenic centers separated by a spacer. The spacer can be virtually any organic compound that is inert to subsequent reactions and is capable of providing the requisite distance between nitrogenic groups so as to effectively crosslink the substrate.

Particularly preferred crosslinking agents are based on alkylene 1,2-bis(4-azidotetrahalobenzoates), which are illustrated below as Formula 1.

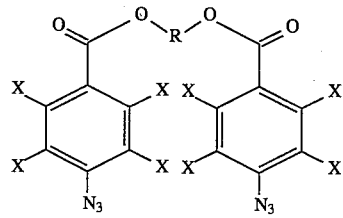

FORMULA 1

R of Formula 1 generally is selected from the group consisting of lower alkyl, lower alkenyl or lower alkynyl groups, particularly lower alkyl groups, wherein "lower" is defined to include carbon chains, both straight and branched chains, having 10 or fewer carbon atoms. X may be selected from the group consisting of halogens, with fluorine being particularly preferred halogen. Formula 1 illustrates the azide groups in the position para to the carboxyl groups. It should be understood that this is illustrative only, and that the azide group or groups can be at other ring positions.

A currently preferred compound useful as a crosslinking agent is ethylene 1,2-bis(4-azido-2,3,5,6-tetraflourobenzoate, shown below as Formula 2.

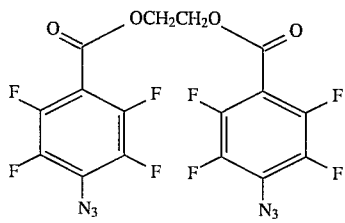

FORMULA 2

C. Functional Monomers

An almost unlimited number of compounds can be used as the functional monomers, although preferred compounds include nitrenogenic centers for the formation of azides. Especially preferred compounds are halophenyl azides, such as illustrated below in Formula 3.

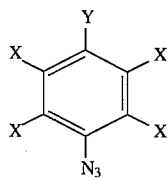

FORMULA 3

Y generally, but not necessarily, is selected from the group consisting of hydroxyl (—OH), lower alkyl alcohols (—ROH), thiols (SH), lower alkyl thiols (—RSH), nitro ($NO_2$), amines (—$NH_3$, —$NHR_1$ —$NR_1R_2$), aldehydes (—CHO), carboxyl acids (—COOH) and esters (COOR). The selection of Y is best determined by considering the imprinting molecule and its ability to interact, either covalently or noncovalently, with the Y group so that the imprinting molecule is held in the substrate during the crosslinking reaction. This is best determined by considering the functional groups present on the imprinting molecule, and then selecting a functional monomer having functional groups capable of interacting, either covalently, or noncovalently, with the functional groups present on the imprinting molecule.

Listed in Table 1 are specific examples, without limitation, of functional monomers that can be used to practice the present invention.

TABLE 1

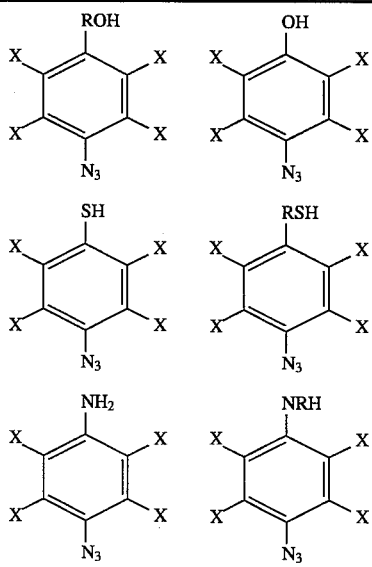

TABLE 1-continued

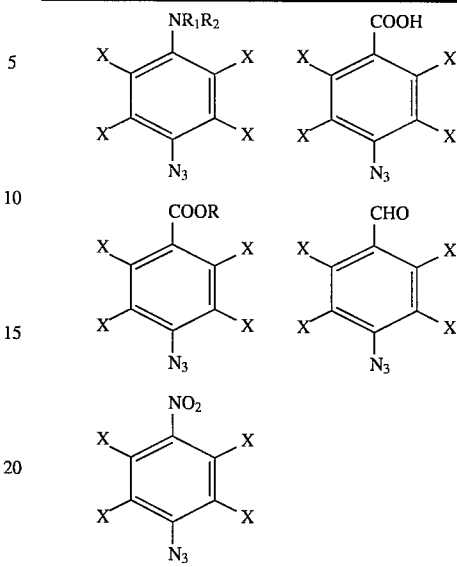

D. Imprinting Molecules

The functional monomers discussed above are selected to interact either covalently or noncovalently with an imprinting molecule. For instance, a working prototype of an imprinted polymeric substrate has used theophylline as the imprinting molecule. Theophylline presumably is coupled to the polymeric substrate by hydrogen bonding. The molecular structure for theophylline is shown below as Formula 4.

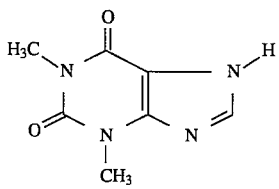

FORMULA 4

However, one skilled in the art will realize that virtually any imprinting molecule can be used to practice the invention by the proper selection of the functional monomer. Listed below in Table 2 are additional examples, without limitation, of compounds that can be used as imprinting molecules for practicing the present invention. Additional examples of such compounds can be found, for instance, in the Merck Index (latest edition) and the Physician's Desk Reference (latest edition), both of which are incorporated herein by reference. Table 2 lists therapeutic agents which can be used as functional monomers. Table 3 lists drugs of abuse, which also can be used as functional monomers.

TABLE 2

| THERAPEUTICS |
|---|
| Acetaminophen |
| Amilacin |
| Amitriptyline |
| Chloramphenicol |
| Cyclosporine |
| Desipramine |
| Digitoxin |
| Digoxin |
| Disopyramide |
| Ethosuximide |
| Flecainide |
| Gentamicin $A_1$, $C_1$, |

TABLE 2-continued

THERAPEUTICS $C_{1a}$, $C_2$, $C_{2b}$
Imipramine
Kanamycin
Lidocaine
Methotrexate
Carbamazepine
N-Acetylprocainamide
(NAPA)
Netilmicin
Nortriptyline
Phenobarbital
Phenytoin
Procainamide
Quinidine
Salicylate
Streptomycin
Theophylline
Tobramycin
Valproic acid
Vancomycin

TABLE 3

DRUGS OF ABUSE

Alcohol
Amphetamines/Methamphetamine
Barbiturates
Benzodiazepine
Buprenorphine
Cannabinoids
Cocaine and metabolites
Fentanyl
LSD
Methadone
Nicotine metabolite
Opiates
Phencyclidine Once the substrate is crosslinked in the presence of both the functional monomer and the imprinting molecule, such as those described above, the imprinting molecule is then removed from the substrate. One skilled in the art will realize that the method for removing the imprinting molecule depends on the nature of the interaction between the imprinting molecule and the functional monomer. If the interaction is covalent, then the covalent bond must be broken. If the interaction is based on hydrogen-bonding, as an example of a noncovalent type of interaction, then the imprinting molecule can be extracted from the crosslinked substrate. In a working prototype, theophylline, apparently hydrogen bonded with a polystyrene polymeric material, has been extracted from a crosslinked substrate with an alcohol/acetic acid mixture.

EXAMPLE 1

This example describes the formation of a molecularly imprinted material using theophylline as the imprinting molecule. A solution comprising the materials, and the amounts thereof, shown below in Table 4 was first formed by dissolving the reagents in about 2.0 mL of xylene.

TABLE 4

| Components | Function | Amount |
|---|---|---|
| polystryrene | polymer substrate | 20.0 mg |
| Ethylene 1,2-bis-(4-azido-2,3,5,6-tetrafluorbenzoate) | crosslinking agent | 6.0 mg |
| 4-azido-2,3,5,6-tetrafluorobenzoic acid | functional monomer | 12.0 mg |
| theophylline | imprinting molecule | 2.2 mg |

Figure 2:
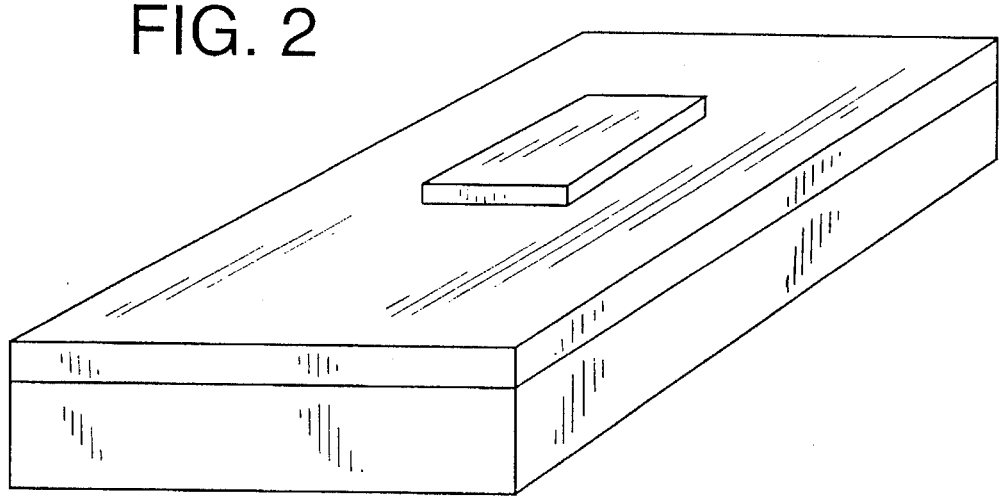
FIG. 2 is a schematic diagram of a strip capacitor and imprinted film according to the present invention.

The fabrication process is illustrated in FIG. 1. The solution comprising the components listed in Table 4 was spin coated onto a silicon wafer at 4000 RPM. This formed a thin film having a thickness of about 20 nm. The film was then baked at 60° C. for 30 minutes and thereafter irradiated at 254 nm for 5 minutes to crosslink the polymeric substrate. A gold thin layer, having an area of about 0.1 cm$^2$ was then evaporated onto the film using a photomask as shown diagramatically in FIG. 2. The imprint molecule was then removed from the substrate by extracting the film with a solution of 9:1 methanol/acetic acid for about 2 minutes to give a molecularly imprinted film having theophylline recognition sites.

In a manner similar to that described in Example 1, imprinting molecules also can be covalently coupled to the substrate. During photolysis to crosslink the substrate, the functional monomer becomes covalently attached to the polymer network. The covalently coupled imprint molecules are then chemically cleaved from the crosslinked substrate to leave an analyte recognition site in the crosslinked substrate. For instance, the functional monomer can be incorporated into the crosslinked substrate by forming, without limitation, esters, ketals, or imines. The formations of such compounds are known by those skilled in the art.

EXAMPLE 2

Figure 3:
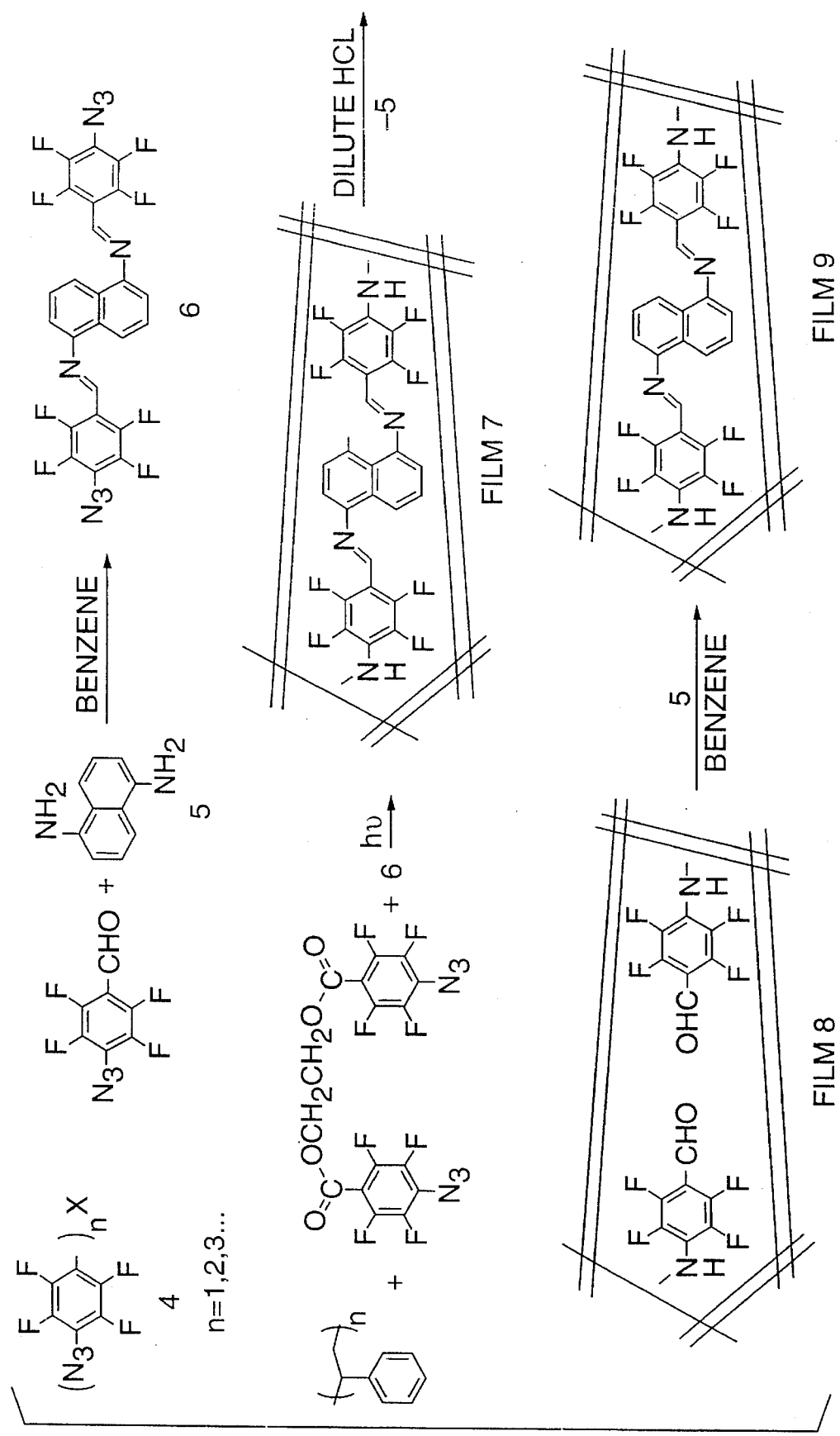
FIG. 3 illustrates one synthetic scheme for covalently linking an imprinting molecule with a film.

A method for covalently coupling an imprinting molecule to a substrate is illustrated in FIG. 3. FIG. 3 shows that an imprinting molecule, such as 1,5-diaminonaphthalene (compound 5 in FIG. 3) is covalently coupled to 4-azidotetrafluorophenyl aldehyde to form imine compound 6. A solution of polystyrene, ethylene 1,2-bis(4-azido-2,3,5,6-tetrafluorobenzoate) and imine compound 6 is then spincoated onto a material, such as a silicon wafer. The residue left following the spincoating is subjected to photolysis to generate the crosslinked film 7, which has imprint molecules covalently attached to the polystyrene. The imine compound can then by hydrolysed using dilute HCl. The acid cleaves the imine and liberates the imprint molecule 1,5-diaminonaphthalene. FIG. 3 also shows that a recognition site for diaminonaphthalene is thus incorporated into the polymeric substrate. Thus, the covalently molecularly imprinted substrate can covalently bind diaminonaphthalene by reversible formation of the amine film 9. In this manner, imprint molecules can be reversibly incorporated into a substrate for the formation of a recognition site in the substrate that corresponds to the molecule used as the imprint molecule.

E. Detecting the Presence of Arialyres With the Imprinted Materials

Once an imprinted film has been produced as described above in Examples 1 and/or 2, the film then can be used to detect the presence of the imprinting molecule. There are a number of ways for detecting the presence of an analyte once it has been brought into contact with the molecularly imprinted material. For instance, and without limitation, the analyte can be detected by: monitoring changes in the capacitance of the film upon interacting with the imprinting molecule; spectroscopic evaluation of the imprinted substrate with imprinting molecule bound thereto, such as by IR, UV, NMR or X-ray photoelectron spectroscopy; and by detecting radiolabelled analytes.

The imprinted substrate prepared as discussed above in Example 1, has been tested to determine whether its presence can be detected by capacitance changes that occur upon interaction with an analyte. This is described below in Example 3.

EXAMPLE 3

An imprinted film was formed as described above in Example 1. The imprinted material was then placed in a solution comprising theophylline in 99:1 acetonitrile/acetic acid for about 10 minutes as illustrated in FIG. 1. The capacitance of this film, as well as a film which did not have an imprinting molecule coupled thereto, was then determined using the silicon wafer and the gold overlay as capacitor plates. The data collected from these capacitance experiments is shown in FIG. 4.

Figure 4:
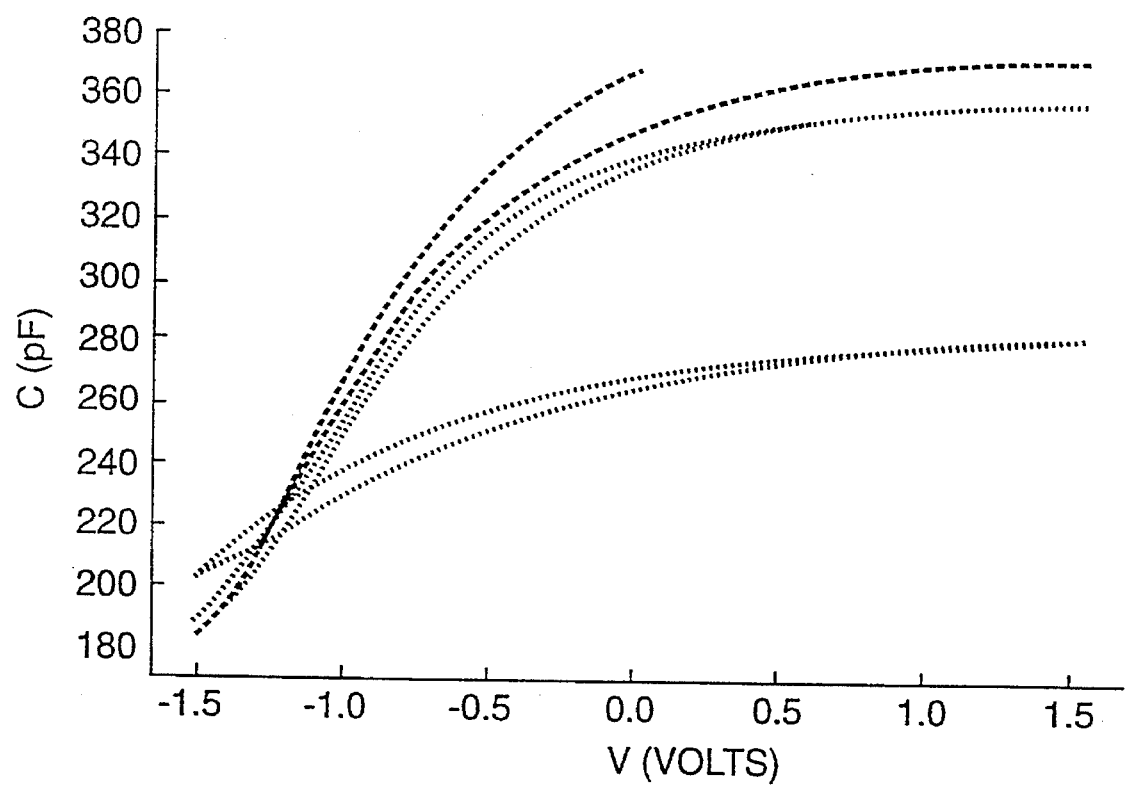
FIG. 4 is a graph showing the capacitance versus bias data for films with and without imprinted molecules coupled thereto.

FIG. 4 includes several curves. Curve a is the capacitance curve for a film that does not have theophylline coupled thereto. Curve b is the capacitance of the film after incubating with a theophylline solution. FIG. 4 clearly shows that the capacitance of the film changes dramatically upon coupling theophylline to the recognition site of the molecularly imprinted film. Thus, by imprinting a film as discussed above, films can be formed for the detection of analytes. A working prototype of a detection film has been made so that the presence of an analyte can be detected by changes in the capacitance of the film once it interacts with the analyte.

Curve c in FIG. 4 is the capacitance of the film after interacting with the analyte. The analyte was then extracted out with methanol and acetic acid as described above. The capacitance of curve c is less than curve b, but higher than curve a. Although this may indicate that the process is not entirely reversible, the results shown in FIG. 4 clearly demonstrate that the analyte can be detected by changes in the capacitance of the film.

This process also can be accomplished using capacitors having small areas made from interdigitated electrodes covered with the imprinted film. This is illustrated schematically in FIG. 5. The electrodes are delineated by standard EB or UV lithography, and are fabricated by thermal evaporation and lift-off procedures. The electrode spacing, thickness and length can be designed to obtain a desired absolute capacitance. Capacitors at least as small as about 1 $\mu m^2$ can be used to practice the invention.

Figure 6A:
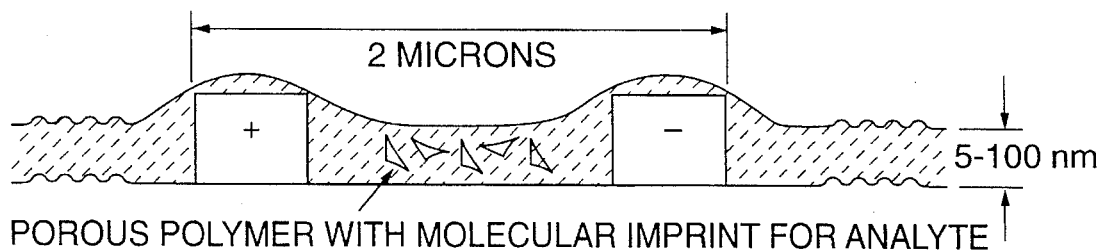
FIG. 6a is a schematic representation of analyte molecules bound to analyte imprinted voids within a substrate.
Figure 6B:
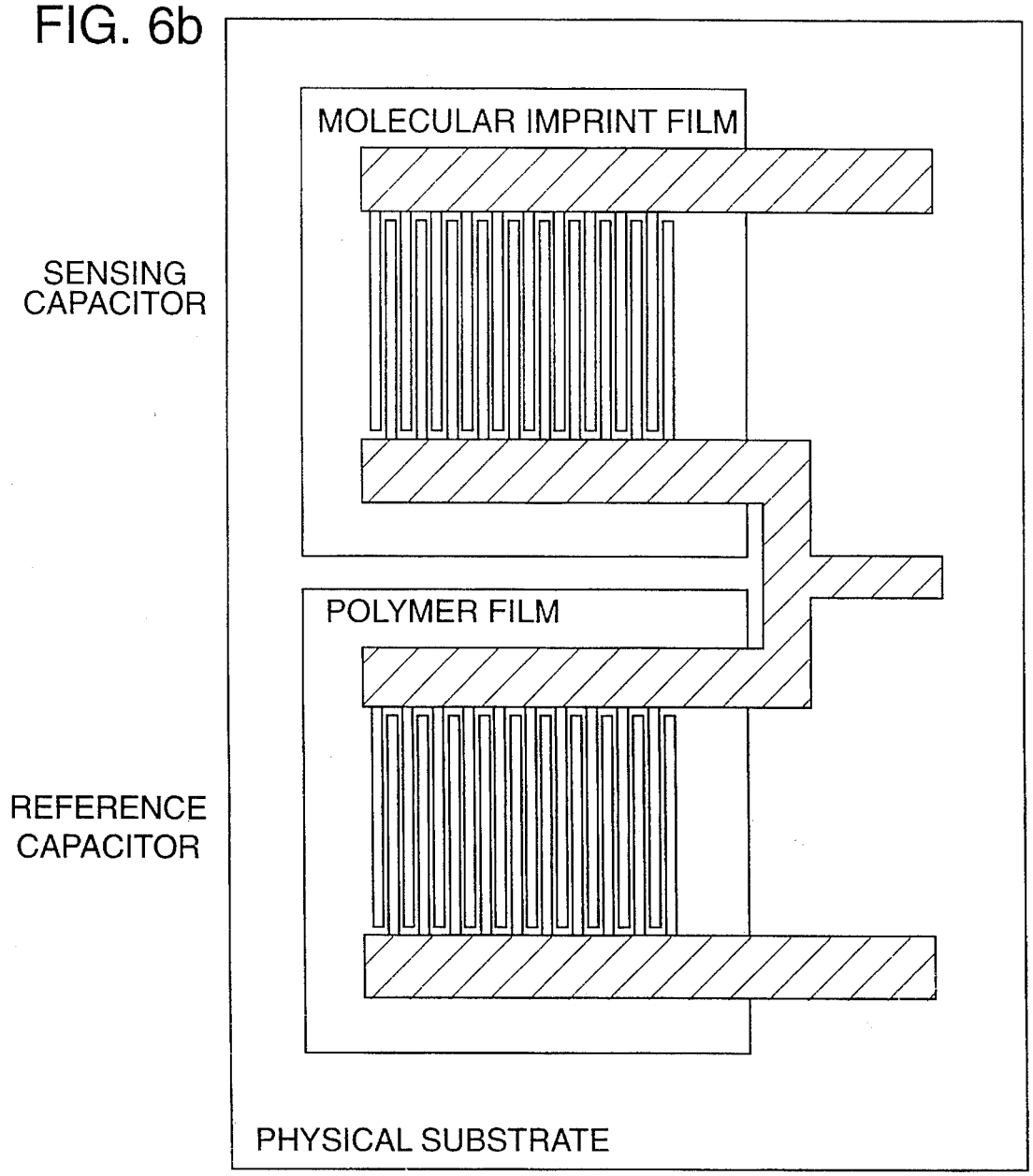
FIG. 6b is a schematic representation of a reference and sensor capacitor/imprinted film.

To form a device which can be used to detect analytes by changes in capacitance, an imprinted polymer is spincoated onto the electrode arrangement for forming the capacitor dielectric, as indicated schematically in FIG. 6a. This allows the chemistry for introducing or removing the imprint molecules to be practiced on the exposed surface of the polymer. Interelectrode capacitance is measured with respect to a second reference interdigitated electrode capacitor on the same physical substrate coated with the same polymer, but without containing recognition sites for the analyte of choice. This is shown schematically In FIG. 6b. Different polymer coatings on two adjacent capacitors can be introduced using UV or EB reaction energy sources to crosslink the polymer in the region of the electrodes. Uncrosslinked material can be removed with an appropriate solvent. The second capacitor is coated by repeating the process with a second polymer film. Sensing measurements are performed on the material after it has been exposed to analytes corresponding to the imprinting molecule. It currently is believed that for a capacitor area of $2.5\times10^{-3}$ $\mu m^2$, and a dielectric thickness of 20 nm, the number of molecules needed to effect the change is $6.5\times10^8$ molecules. This corresponds to about 0.2 pg of theophylline. In other words, the imprinted films can be used to detect very minute quantities of analyte. The absolute capacitance of the small capacitors will be about 100 pF and a 1–10% change is readily detectable using standard techniques. The response time for such devices will be quite quick, on the order of about 50 ms.

In a manner similar to that described above for capacitance measurements, the presence of an analyte also can be detected by means other than capacitance, such as the spectroscopic detection methods listed above. For instance, a molecularly imprinted film can be formed, and the imprinting molecule removed. The imprinted substrate can then be coupled with the analyte used as the imprinting molecule. The interaction of the imprinted film with the analyte can then be determined by subjecting the film to spectroscopic analysis, such as, without limitation, Fourier Transform IR analysis.

Figure 5:
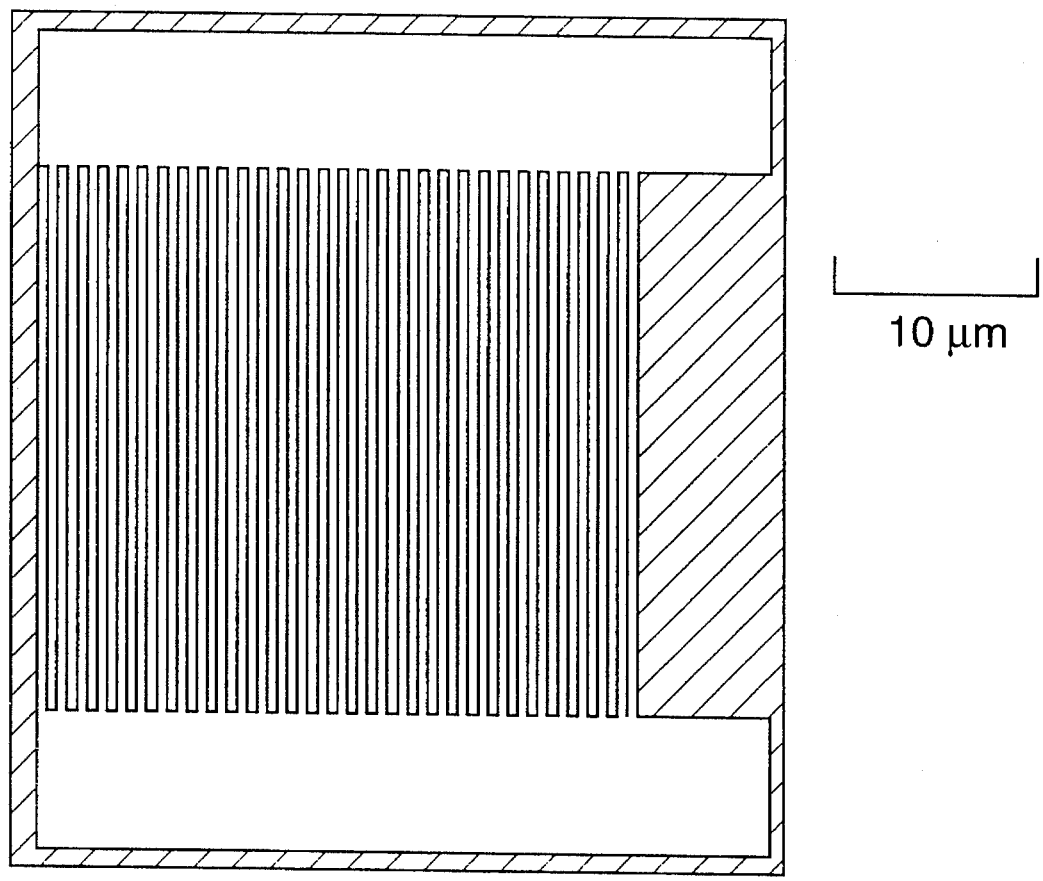
FIG. 5 is a schematic drawing showing a capacitor having interdigitated electrodes for use with the present invention.

A sensor for detecting multiple analytes can thus be made using the imprinted films described above. The sensor most likely would be constructed using films having recognition sites for plural analytes. For instance, a polymeric film could be formed having recognition sites for a variety of analytes, such as, without limitation, those listed in Tables 2 and 3. The imprinted films would be coupled with a means for detecting the presence of an analyte once it is coupled to the recognition site. For instance, an interdigitated capacitance sensor could be formed as shown in FIGS. 5 and 6. When the recognition sites are coupled to the appropriate analyte, the capacitance of the film will change. This capacitance change can be detected using known techniques. The sensor also could employ other known means for detecting analytes, in combination with the imprinted films of the present invention. And, the sensor could be produced so that the films can reversibly bind analytes, or the sensor could be formed so that the films couple the analytes nonreversibly. In this case, the sensor likely would be a disposable device, or the imprinted-film portion of the device could be replaced with a new imprinted film following a first use of the device. Alternatively, the device could include plug-in modules, each of which modules is particularly useful for the detection of a particular analyte, or a particular group of plural analytes.

The present invention has been described in accordance with preferred embodiments. However, it will be understood that certain substitutions and alterations may be made thereto without departing from the spirit and scope of the following claims.

We claim:

1. A method for molecularly imprinting a material, comprising:

forming a solution comprising a solvent and (a) a polymeric material capable of undergoing an addition reaction with a nitrene, (b) a crosslinking agent, (c) a functionalizing monomer, and (d) an imprinting molecule;

evaporating the solvent to leave a residue;

exposing the residue to an energy source, thereby forming a crosslinked polymeric substrate; and extracting the imprinting molecule from the crosslinked polymeric substrate.

2. The method according to claim 1 wherein the crosslinking agent satisfies the formula

[structure: bis(azido-tetrahalo-benzoate) with bridging O–R–O group]

wherein X is a halogen and R is lower alkyl.

3. The method according to claim 2 wherein X is fluorine.

4. The method according to claim 1 wherein the functionalizing monomer satisfies the formula

[structure: benzene ring with Y at top, X at 2,3,5,6 positions, and $N_3$ at para position]

wherein X is a halogen and Y is selected from the group consisting of —OH, —ROH, —SH, —RSH, —CHO, —COOH, COOR, $NO_2$, —$NH_3$, —$NHR_1$ and —$NR_1R_2$.

5. The method according to claim 4 wherein X is fluorine.

6. The method according to claim 5 wherein Y is —COOH.

7. The method according to claim 1 wherein the imprinting molecule is

[structure: theophylline-like molecule with $H_3C$–N, C=O, N–$CH_3$, and N–H groups]

8. The method according to claim 1 wherein the step of evaporating further comprises spincoating a surface of a silicon wafer with the solution.

9. The method according to claim 1 wherein the exposing step comprises exposing the residue to ultraviolet light or an electron beam.

10. The method according to claim 1, wherein the imprinting molecule is selected from the group consisting of acetaminophen, amilacin, amitriptyline, chloramphenical, cyclosporine, desipramine, digitoxin, digoxin, disopyramide, ethosuximide, flecainide, gentamicin, imipramine, hanamycin, lidocaine, methotrexate, carbamazepine, N-acetylprocainamide, metilmicin, nortriptyline, phenobarbital, phenytoin, procainamide, quinidine, salicylate, streptomycin, theophylline, tobramycin, valproic acid, vancomycin, ethanol, amphetamines, barbiturates, benzodiazepine, buprenorphine, cannabinoids, cocaine, cocaine metabolites, fentanyl, lysergic acid diethylamide, methadone, nicotine, nicotine metabolites, opiates and phencyclidine.

11. A method for molecularly imprinting a material, comprising:
forming a solution comprising a solvent and (a) a polymeric material capable of undergoing an addition reaction with a nitrene, (b) a crosslinking agent according to the formula

[structure: bis(azido-tetrahalo-benzoate) with bridging O–R–O group]

wherein R is a lower alkyl group and X is a halogen, (c) a functionalizing monomer according to the formula

[structure: benzene ring with Y at top, X at 2,3,5,6 positions, and $N_3$ at para position]

wherein X is a halogen and Y is selected from the group consisting of —OH, —SH, —CHO, —COOH, —$NH_3$, —$NHR_1$ and —$NR_1R_2$, and (d) an imprinting molecule;
evaporating the solvent to leave a residue;
exposing the residue to an energy source to form a crosslinked polymeric substrate; and
extracting the imprinting molecule from the crosslinked polymeric substrate.

12. The method according to claim 11 wherein the polymeric substrate includes chemical moieties selected from a group consisting of —CH, —NH, —OH, —C—C—, —C=C—, SiO—H, Si—OH, and Si—OSi moieties.

13. The method according to claim 11 wherein the polymeric material is selected from the group consisting of saturated polyolefins, acrylics, polystyrene, polystyrene analogs, unsaturated polyolefins, polyimides, polyesters, conjugated polymers, conducting polymers, inorganic polymers, organic metals, organometallic polymers, and polysaccharides.

14. The method according to claim 11 wherein the X of the crosslinking agent is fluorine.

15. The method according to claim 11 wherein the crosslinking agent is ethylene 1,2-bis(4-azido-2,3,5,6-tetrafluorobenzoate).

16. The method according to claim 11 wherein X of the functionalizing monomer is fluorine.

17. The method according to claim 11 wherein the functionalizing monomer is 4-azido-2,3,5,6-tetraflourobenzoic acid.

18. The method according to claim 11 wherein the imprinting molecule is

[structure: theophylline-like molecule with $H_3C$–N, C=O, N–$CH_3$, and N–H groups]

19. The method according to claim 11 wherein the step of evaporating the solvent comprises spincoating a silicon wafer with the solution to form a film, and the exposing step comprises exposing the film to an energy source.

20. The method according to claim 11 wherein the energy source is selected from a group consisting of energized electrons, energized ions, photons, and heat.

21. The method according to claim 11 wherein the exposing step comprises exposing preselected regions on the polymeric material to the energy source so as to create a pattern of functionalized regions on the surface relative to non-functionalized regions.

22. The method according to claim 11 wherein the energy source is photons.

23. The method according to claim 22 wherein the energy source is ultraviolet light.

24. The method according to claim 11, wherein the imprinting molecule is selected from the group consisting of acetaminophen, amilacin, amitriptyline, chloramphenical, cyclosporine, desipramine, digitoxin, digoxin, disopyramide, ethosuximide, flecainide, gentamicin, imipramine, hanamycin, lidocaine, methotrexate, carbamazepine, N-acetylprocainamide, metilmicin, nortriptyline, phenobarbital, phenytoin, procainamide, quinidine, salicylate, streptomycin, theophylline, tobramycin, valproic acid, vancomycin, ethanol, amphetamines, barbiturates, benzodiazepine, buprenorphine, cannabinoids, cocaine, cocaine metabolites, fentanyl, lysergic acid diethylamide, methadone, nicotine, nicotine metabolites, opiates and phencyclidine.

25. A method for molecularly imprinting a material, comprising:

forming a solution comprising a solvent and (a) a polymeric material capable of undergoing an addition reaction with a nitrene, (b) a crosslinking agent according to the formula

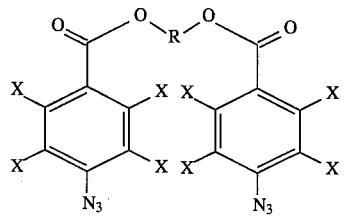

wherein R is a lower alkyl group and X is a halogen, (c) a functionalizing monomer according to the formula

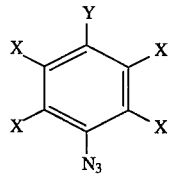

wherein X is a halogen and Y is selected from the group consisting of —OH, —SH, —CHO, —COOH, —NH₃, —NHR₁ and —NR₁R₂, and (d) an imprinting molecule;

coating a silicon wafer with the solution;
evaporating the solvent to form a film on the silicon wafer;
exposing the film to an energy source; and
extracting the imprinting molecule from the film.

26. The method according to claim 25 wherein the polymeric material is selected from the group consisting of saturated polyolefins, acrylics, polystyrene, polystyrene analogs, unsaturated polyolefins, polyimides, polyesters, conjugated polymers, conducting polymers, inorganic polymers, organic metals, organometallic polymers, and polysaccharides.

27. The method according to claim 25 wherein the crosslinking agent is ethylene 1,2-bis(4-azido-2,3,5,6-tetrafluorobenzoate).

28. The method according to claim 25 wherein the functionalizing monomer is 4-azido-2,3,5,6-tetraflourobenzoic acid.

29. The method according to claim 25 wherein the imprinting molecule is

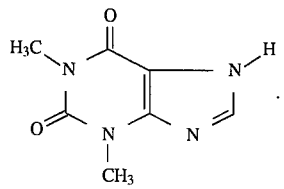

30. The method according to claim 25, wherein the imprinting molecule is selected from the group consisting of acetaminophen, amilacin, amitriptyline, chloramphenical, cyclosporine, desipramine, digitoxin, digoxin, disopyramide, ethosuximide, flecainide, gentamicin, imipramine, hanamycin, lidocaine, methotrexate, carbamazepine, N-acetylprocainamide, metilmicin, nortriptyline, phenobarbital, phenytoin, procainamide, quinidine, salicylate, streptomycin, theophylline, tobramycin, valproic acid, vancomycin, ethanol, amphetamines, barbiturates, benzodiazepine, buprenorphine, cannabinoids, cocaine, cocaine metabolites, fentanyl, lysergic acid diethylamide, methadone, nicotine, nicotine metabolites, opiates and phencyclidine.

31. A method for molecularly imprinting a material, comprising:

forming a solution comprising a solvent and (a) a polymeric material capable of undergoing an addition reaction with a nitrene selected from the group consisting of saturated polyolefins, acrylics, polystyrene, polystyrene analogs, unsaturated polyolefins, polyimides, polyesters, conjugated polymers, conducting polymers, inorganic polymers, organic metals, organometallic polymers, and polysaccharides, (b) a crosslinking agent according to the formula

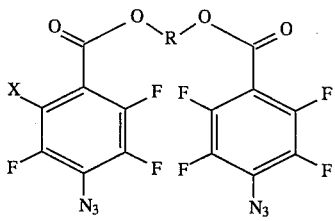

wherein R is a lower alkyl group, (c) a functionalizing monomer according to the formula

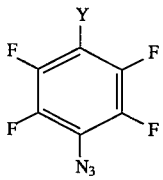

wherein Y is selected from the group consisting of —OH, —SH, —CHO, —COOH, —NH₃, —NHR₁ and —NR₁R₂, and (d) an imprinting molecule;
spincoating a silicon wafer with the solution;
evaporating the solvent to form a film on the silicon wafer;
exposing the film to an energy source selected from the group consisting of energized electrons, energized ions, photons and heat; and extracting the imprinting molecule from the film.

32. The method according to claim 31 wherein the crosslinking agent is ethylene 1,2-bis(4-azido-2,3,5,6-tetrafluorobenzoate).

33. The method according to claim 32 wherein the functionalizing monomer is 4-azido-2,3,5,6-tetraflourobenzoic acid.

34. The method according to claim 31 wherein the imprinting molecule is

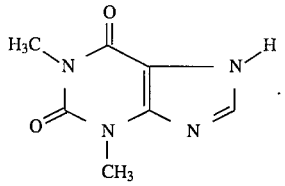

35. The method according to claim 31, wherein the imprinting molecule is selected from the group consisting of acetaminophen, amilacin, amitriptyline, chloramphenical, cyclosporine, desipramine, digitoxin, digoxin, disopyramide, ethosuximide, flecainide, gentamicin, imipramine, hanamycin, lidocaine, methotrexate, carbamazepine, N-acetylprocainamide, metilmicin, nortriptyline, phenobarbital, phenytoin, procainamide, quinidine, salicylate, streptomycin, theophylline, tobramycin, valproic acid, vancomycin, ethanol, amphetamines, barbiturates, benzodiazepine, buprenorphine, cannabinoids, cocaine, cocaine metabolites, fentanyl, lysergic acid diethylamide, methadone, nicotine, nicotine metabolites, opiates and phencyclidine.

36. A method for detecting an analyte, comprising:

forming solutions comprising (a) a substrate capable of undergoing an addition reaction with a nitrene, (b) a crosslinking agent according to the formula

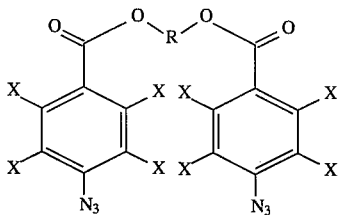

wherein R is a lower alkyl group and X is a halogen, (c) a functionalizing monomer according to the formula

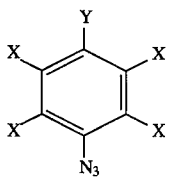

wherein X is a halogen and Y is selected from the group consisting of —OH, —SH, —CHO, —COOH, —NH$_3$, —NHR$_1$ and —NR$_1$R$_2$, and (d) an imprinting molecule;

evaporating the solvent to form a film;

exposing the film to a reaction energy to form a crosslinked substrate;

extracting the imprinting molecules from the crosslinked substrate;

exposing the film to one or more of the imprinting molecules for a period of time sufficient to couple the imprinting molecules to the film; and detecting the presence of the imprinting molecule.

37. The method according to claim 36 wherein the step of detecting the imprinting molecule comprises measuring the capacitance of the film after the exposing step.

38. The method according to claim 36 wherein the step of detecting the imprinting molecule comprises measuring light characteristics of the film.

39. A molecularly imprinted polymeric material comprising a polymeric substrate crosslinked in the presence of an imprinting molecule with a crosslinking agent according to the formula

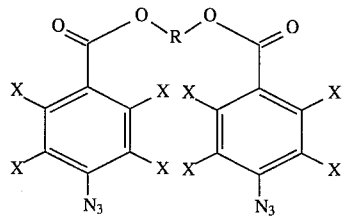

and further including a functionalizing molecule according to the formula

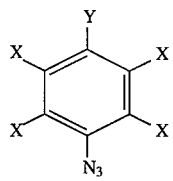

40. The method according to claim 36, wherein the imprinting molecule is selected from the group consisting of acetaminophen, amilacin, amitriptyline, chloramphenical, cyclosporine, desipramine, digitoxin, digoxin, disopyramide, ethosuximide, flecainide, gentamicin, imipramine, hanamycin, lidocaine, methotrexate, carbamazepine, N-acetylprocainamide, metilmicin, nortriptyline, phenobarbital, phenytoin, procainamide, quinidine, salicylate, streptomycin, theophylline, tobramycin, valproic acid, vancomycin, ethanol, amphetamines, barbiturates, benzodiazepine, buprenorphine, cannabinoids, cocaine, cocaine metabolites, fentanyl, lysergic acid diethylamide, methadone, nicotine, nicotine metabolites, opiates and phencyclidine.

41. The method according to claim 39 wherein the polymeric material is selected from the group consisting of saturated polyolefins, acrylics, polystyrene, polystyrene analogs, unsaturated polyolefins, polyimides, polyesters, conjugated polymers, conducting polymers, inorganic polymers, organic metals, organometallic polymers, and polysaccharides.

42. The method according to claim 39 wherein X of the crosslinking agent is fluorine.

43. The method according to claim 39 wherein the crosslinking agent is ethylene 1,2-bis(4-azido-2,3,5,6-tetrafluorobenzoate).

44. The method according to claim 39 wherein X of the functionalizing monomer is fluorine.

45. The method according to claim 39 wherein the functionalizing monomer is 4-azido-2,3,5,6-tetraflourobenzoic acid.

46. A sensor employing the molecularly imprinted material of claim 39.

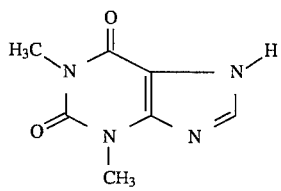

47. The material according to claim 39, wherein the imprinting molecule is selected from the group consisting of acetaminophen, amilacin, amitriptyline, chloramphenical, cyclosporine, desipramine, digitoxin, digoxin, disopyramide, ethosuximide, flecainide, gentamicin, imipramine, hanamycin, lidocaine, methotrexate, carbamazepine, N-acetylprocainamide, metilmicin, nortriptyline, phenobarbital, phenytoin, procainamide, quinidine, salicylate, streptomycin, theophylline, tobramycin, valproic acid, vancomycin, ethanol, amphetamines, barbiturates, benzodiazepine, buprenorphine, cannabinoids, cocaine, cocaine metabolites, fentanyl, lysergic acid diethylamide, methadone, nicotine, nicotine metabolites, opiates and phencyclidine.

* * * * *